United States Patent [19]
Abbott, III et al.

[11] Patent Number: 5,396,323
[45] Date of Patent: Mar. 7, 1995

[54] METHOD AND APPARATUS FOR ANALYZING OPTICAL WAVEGUIDE CANE

[75] Inventors: John S. Abbott, III, Elmira, N.Y.; Donald L. Knasel, Wilmington, N.C.; David A. Pastel, Corning; Bruce W. Reding, Elmira, both of N.Y.; Gregory E. Smith, Wilmington, N.C.

[73] Assignee: Corning Incorporated, Corning, N.Y.

[21] Appl. No.: 192,357

[22] Filed: Feb. 7, 1994

[51] Int. Cl.$^6$ ............................................. G01N 21/41
[52] U.S. Cl. .................................................. 356/73.1
[58] Field of Search ........................................ 356/73.1

[56] References Cited

U.S. PATENT DOCUMENTS

| 4,181,433 | 1/1980 | Marcuse | 356/73.1 |
| 4,227,806 | 10/1980 | Watkins | 356/73.1 |
| 4,726,677 | 2/1988 | Glantschnig et al. | 356/73.1 |

FOREIGN PATENT DOCUMENTS

| 0085981 | 8/1983 | European Pat. Off. . |
| 0096829 | 12/1983 | European Pat. Off. . |

OTHER PUBLICATIONS

P. L. Chu, "Nondestructive Measurement of Index Profile of an Optical-Fibre Preform", *Electronics Letters*, vol. 13, No. 24, Nov. 24, 1977, pp. 736–738.

D. Marcuse, *Principles of Optical Fiber Measurements*, pp. 150–167, Academic Press, New York, 1981.

M. G. Blankenship et al., "The Outside Vapor Deposition Method of Fabricating Optical Waveguide Fibers", *IEEE Journal of Quantum Electronics*, vol. QE-18, No. 10, Oct. 1982, pp. 1418–1423.

W. J. Stewart, "Optical Fiber and Preform Profiling Technology", *IEEE Journal of Quantum Electronics*, vol. QE-18, No. 10, Oct. 1982, pp. 1451–1466.

W. J. Glantschnig, "How Accurately Can One Reconstruct an Index Profile from Transverse Measurement Data?", *IEEE Journal of Lightwave Technology*, vol. LT-3, No. 3, Jun. 1985, pp. 678–683.

Product Brochure for P102 Preform Analyzer, York Technology Inc., Sep. 1988.

Operator's manual for P104 Preform Analyser, York Technology Ltd., May 1992, p. 1.8.

*Primary Examiner*—Vincent P. McGraw
*Attorney, Agent, or Firm*—Bruce E. Kamerer

[57] ABSTRACT

A method and apparatus for non-destructive analysis of canes and preforms which contain "striae" in which the cane or preform is transversely illuminated with a beam of light at a wavelength which is long enough to substantially eliminate the effect of striae resulting from variations in dopant concentration.

8 Claims, 3 Drawing Sheets

METHOD AND APPARATUS FOR ANALYZING OPTICAL WAVEGUIDE CANE

This invention relates to a nondestructive method for analyzing cane which is to be overclad and drawn into optical waveguide fiber and an apparatus for performing the analysis.

BACKGROUND OF THE INVENTION

In the manufacture of optical waveguide fiber, it has become increasingly important to produce low-cost, high quality fiber. A typical design for optical fiber uses a core region of silica doped with refractive index modifiers surrounded by a cladding region of undoped silica. The outside diameter of the cladding is typically 125 $\mu m$, with the core region of a singlemode fiber being about 8–10 $\mu m$ in diameter and the core region of a multimode fiber being about 50–62.5 $\mu m$ in diameter. The equipment used to produce the doped silica is generally more complex than the equipment used to produce the undoped silica because of the need to control the dopant concentration, although both types of equipment must be capable of producing high quality product which is substantially free of impurities.

One method of reducing the production cost of optical fiber is to use a "two step" process for the manufacture of preforms which are drawn into fiber. The process comprises the following steps:

a. produce a core soot preform which contains all of the doped silica core region and, preferably, a small portion of the cladding region;
b. dehydrate and consolidate the core soot preform;
c. draw core canes from the consolidated core soot preform;
d. overclad the core cane with undoped silica which forms the remainder of the cladding region;
e. dehydrate and consolidate the overclad soot preform; and
f. draw the consolidated overclad preform into fiber and apply protective coating.

Because the equipment used to produce the overclad preform can be substantially less complex than the equipment used to produce the core preform, the overall cost of manufacturing fiber can be reduced. A process as described above can be employed advantageously to produce both singlemode and multimode fiber, although the economic advantages are greater in the case of singlemode fiber because of the greater proportion of cladding region relative to core region in the resulting fiber. The two step process is compared to a "one step" process in which a soot preform containing both the core and complete cladding regions is deposited, dehydrated and consolidated, and drawn into fiber.

In fiber manufacturing processes, measurements of optical properties are generally made after the fiber is drawn. These measurements of optical properties provide information which is used to adjust the manufacturing process steps to improve or maintain optical characteristics of the fiber. However, in the two step process noted above, this "feedback" can be delayed by the extra steps involved in making the core and overclad preforms (steps c through e) as compared to the more traditional fiber process of making a single preform which forms the entire core and cladding regions of the fiber when drawn. Also, if optical property problems can be detected prior to overcladding the core cane, dehydrating and consolidating the overclad preform, drawing and coating the fiber, the significant cost of these steps can be avoided, and only the defective core cane or preform is discarded. Additionally, the information obtained by measuring the core preform or cane can be useful in adjusting the subsequent processing steps to provide fiber with particular characteristics.

It is desirable, therefore, to have methods and apparatus for measuring the optical properties of either consolidated preforms and/or core canes drawn therefrom. The methods and apparatus used should generally be nondestructive and provide quick and easy analysis of the preforms and/or canes. There are a number of commercially available analyzers which are capable of providing quick and accurate measurements of core cane. These measurements are used by manufacturing personnel to reject defective canes before subsequent processing as well as to predict the correct amount of overcladding to apply to the core cane in the subsequent step of forming an overclad soot preform. Representative of these devices are models P-102 and P-104 Preform Analyzers, which are available from York Technology Ltd. of Chandler's Ford, Hampshire, England. These devices typically operate at wavelengths of about 632 nm, although wavelengths in the range of 632 to 900 nm have also been used.

The key optical parameter for multimode fiber is the bandwidth. Bandwidth, which is specified at specific operating wavelengths, is a measure of the data capacity of a fiber. The larger the bandwidth at a given wavelength, the greater the data capacity. The bandwidth of a multimode fiber is highly dependent on the refractive index profile of the fiber. In order to achieve the highest bandwidth, the refractive index profile must be closely controlled to obtain, as nearly as possible, the optimum profile shape.

The refractive index profile of a fiber is determined primarily during the step of producing the core soot preform (step a in the process outline above), although there are other process steps after producing the core soot preform which can have some impact on the refractive index profile of the resulting fiber.

Numerous methods have been proposed for analyzing the refractive index profile of optical waveguide preforms. These include axial as well as transverse methods. Axial methods are most applicable to profiling fibers rather than preforms because of the requirements to have flat perpendicular ends on the fiber or preform or, in the case of axial interferometric methods, a thin slice cut from the fiber or preform. Transverse methods are generally nondestructive which is of particular consequence when analyzing preforms. For a summary of both axial and transverse profiling techniques, see, W. J. Stewart, "Optical Fiber and Preform Profiling Technology", IEEE J. of Quantum Elec., vol. QE-18, no. 10, pp. 1451–1466, October 1982.

Transverse profiling techniques generally require sophisticated algorithms to reconstruct a refractive index profile. See, for example, W. J. Glantschnig, "How Accurately Can One Reconstruct an Index Profile From Transverse Measurement Data?", J. of Lightwave Tech., vol. LT-3, no. 3, pp. 678–683, June 1985. Also, the various transverse methods suffer from spatial resolution limitations and require complex apparatus to provide transverse measurement data. See, Stewart, pp. 1461–1464.

The measurement methodology for transverse profiling techniques is described with reference to FIG. 1(a). Wavefront 1 is passed transversely through sample 2, which can be either a preform, cane or fiber. Because of differential phase delays caused by the varying refractive index along the sample radius, indicated by arrow 3, wavefront 1 becomes distorted wavefront 4 after passing through the sample. Various transverse profiling methods measure either the phase delay, as indicated by the curved section 5 of distorted wavefront 4, or, alternatively, the ray bending, as indicated by arrows 6.

One transverse profiling technique known as the beam deflection technique is described with reference to FIG. 1(b). A focused beam of light 11 is transversely incident on sample 12 at a distance x from the sample axis 13 and passes through sample 12. Beam 11 is deflected as it passes through sample 12 because of the refractive index of sample 12. Beam 13 is detected by detector 14 at a distance y from the sample axis. Beam 11 is then indexed across sample 12 as shown by arrow 15. The deflection data, y, is collected as a function of x, the position of beam 11 from the radius of sample 12. Mathematical deconvolution of the deflection data as a function of beam position is used to reconstruct the refractive index profile of the sample. Collection of the data and the subsequent mathematical manipulation is typically done using a computer.

A significant impediment to the accurate determination of the refractive index profile of preforms and core canes is the structure of index striae in a consolidated preform. Index striae result from refractive index variations within layers as the preforms are formed. Index striae can result in preforms made by any of the techniques used in the commercial production of optical fibers, including the outside vapor deposition (OVD), modified chemical vapor deposition (MCVD), plasma-enhanced chemical vapor deposition (PECVD) and vapor axial deposition (VAD) methods. The striae can occur in singlemode, multimode or dispersion-shifted preforms and canes.

In the OVD method, the refractive index profile is determined by the temperature at which soot is deposited as well as the flow rates of the refractive index dopants, such as $GeO_2$, during the soot deposition step. The soot is deposited along the length of a rotating target in successive layers. Further details on the OVD method may be found in M. G. Blankenship et at., "The Outside Vapor Deposition Method of Fabricating Optical Waveguide Fibers", IEEE J. of Quantum Elec., vol. QE-18, no. 10, pp. 1418-23, October 1982.

The index striae cause a complicated deflection pattern to be generated when known methods of profiling preforms and core canes are used. The degree to which the striae will adversely affect the ability to analyze a cane or preform depends on: (a) the spacing of the striae, and (b) the amplitude of the striae. While the striae are present in varying degrees in preforms and canes made by all known manufacturing processes, the striae appear to have a greater effect in preforms and canes manufactured by the OVD method and is particularly problematic for multimode preforms and canes made by the OVD method.

SUMMARY OF THE INVENTION

It is an object of this invention to provide a nondestructive method for determining the refractive index profile of optical fiber preforms and core canes.

In order to achieve this and other objects, a method is provided wherein the wavelength of the beam, for which deflection data is collected on an optical fiber preform or core cane, is selected based on the structure of the index striae.

DETAILED DESCRIPTION

Figure 1A:
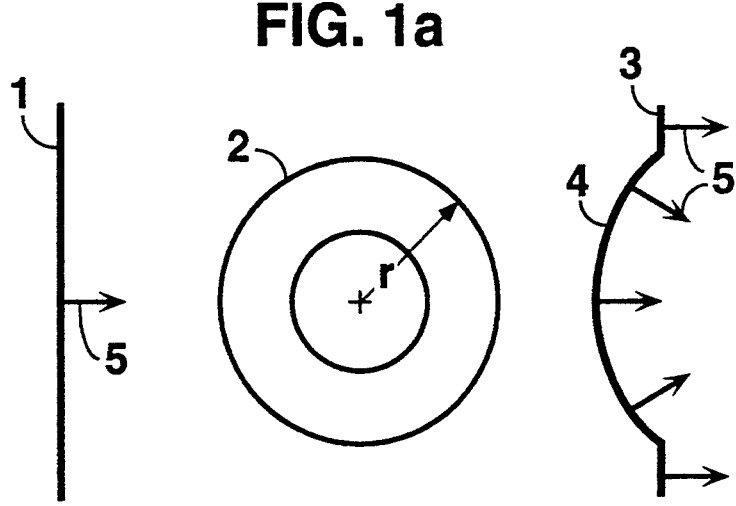
FIG. 1(a) shows the effect on a wavefront traversing an optical fiber, cane or preform.
Figure 1B:
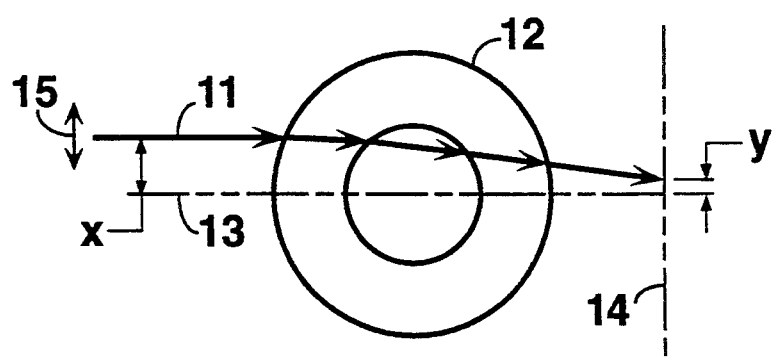
FIG. 1(b) shows one typical method of transverse beam deflection profile measurement.
Figure 2:
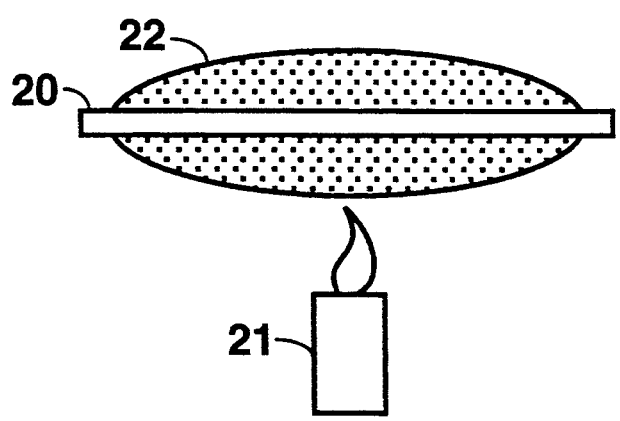
FIG. 2 shows a typical OVD laydown process.

In the OVD method of producing optical waveguides, soot deposition typically occurs by oxidizing-/hydrolyzing materials containing precursors for the base silica glass and any refractive index modifying materials, such as $GeO_2$, to produce a soot material which is collected to form a soot preform. As shown in FIG. 2, the soot deposition process typically includes a rotating target rod 20 and soot deposition burner 21. There is relative translational movement of burner 21 along the length of rod 20 such that soot 22 is substantially evenly distributed along the length of rod 20. Optionally, multiple soot deposition burners may be utilized, and rod 20 may be oriented horizontally or vertically, with corresponding orientation of the burner(s).

The OVD method for making soot preforms results in layers of soot being applied sequentially to rod 20 to form the soot preform. These sequential layers typically have continuously varying compositions especially in the portion of the preform which becomes the core region of the resulting fiber. The different composition of the various layers is controlled to produce a specific refractive index profile within the core region of the fiber. The bandwidth of a multimode fiber is critically dependent on controlling the refractive index profile such that it substantially matches a desirable optimum shape.

Regardless of the method of manufacture, striae of different composition are produced within the consolidated preform which result from relatively large variations of dopant content within a layer of soot. While these striae are present in singlemode, multimode or dispersion-shifted fiber preforms manufactured by the OVD, MCVD, PECVD, or VAD methods, the index striae structure in multimode preforms and canes produced by the OVD method make the commercially available analyzers unsuitable for non-destructive analysis of multimode preforms and canes produced by the OVD method unless the multimode cane has a relatively small diameter. However, small diameters of cane would reduce or eliminate the efficiency gains of the two step process and are, therefore, impractical for commercial use.

Figure 3:
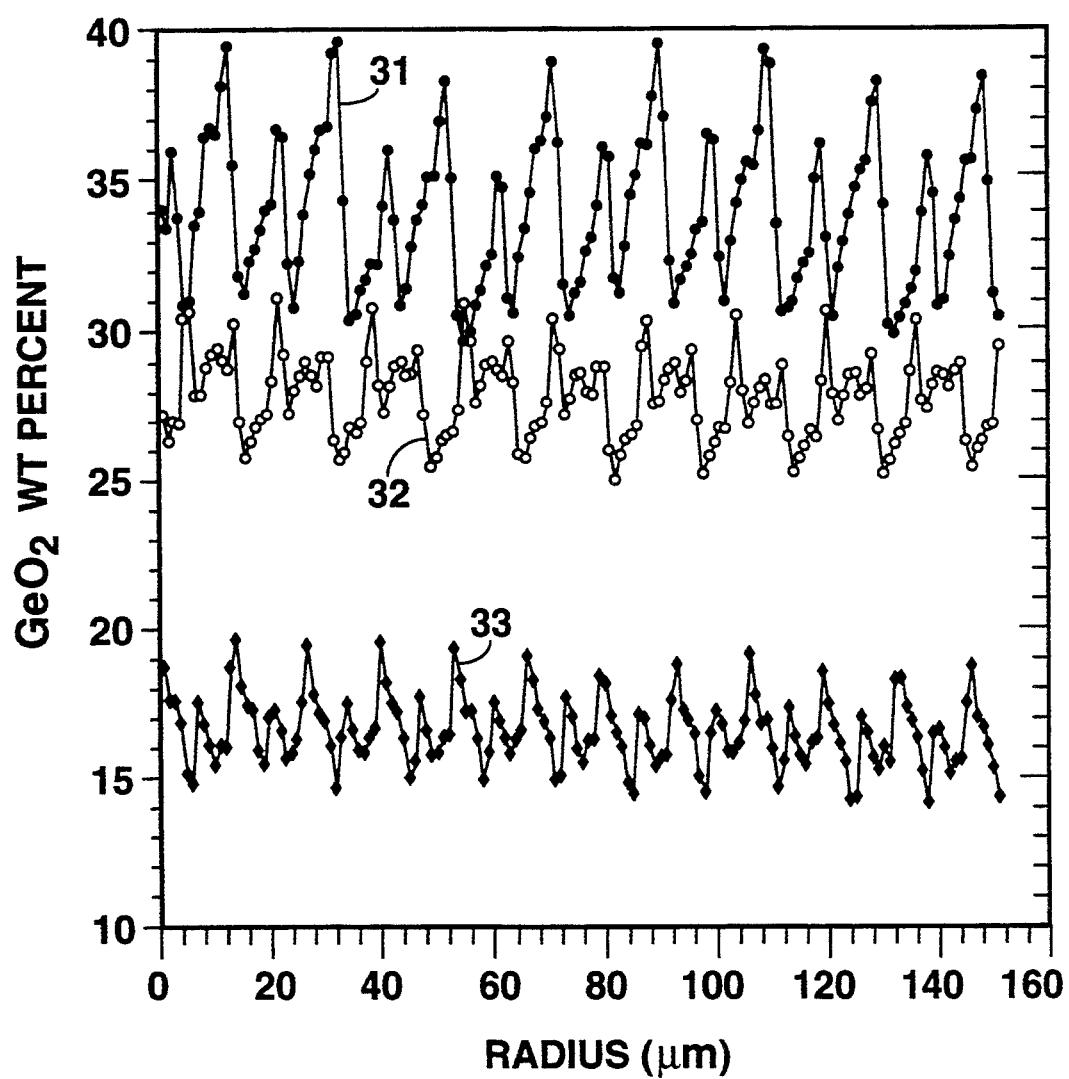
FIG. 3 shows the striae produced in a cane drawn from a preform produced by the OVD method.

The striae are illustrated in FIG. 3 which is a graphical representation of a microprobe analysis of a cane which was drawn from a preform produced by the OVD method. Curves 31, 32, and 33 represent the $GeO_2$ concentrations, in wt. %, at approximately 25%, 50%, and 75% of the fiber radius from the center of the fiber, respectively.

Mathematical modeling of the transmission of a beam of light through a cane indicates that a combination of diffractive and refractive effects influence the light. The diffractive effect depends on the ratio of the wavelength of the light to the striae spacing and changes as the wavelength (or the cane diameter) changes. The refractive effect depends on the bending of light rays by the variable index medium of the cane.

The index profile of a cane is calculated by measuring the deflection of a beam of light as it passes transversely through the cane. The calculations used to construct the refractive index profile from the deflection data associate the amount of deflection with the refraction which occurred. These calculations assume that the deflection is caused entirely by refraction.

More specifically, the deflection function, $z_0(x)$, is the exit angle, $z_0$, of a beam of light which entered the cane at position x. The deflection pattern, $I(x,z)$, is the intensity of light at exit angle z for the beam of light that entered the cane at position x. When the deflection pattern is dominated by a single primary lobe, $I_{primary}(x,z_0)$, which traces out the deflection function, $z_0(x)$, the calculation of the refractive index profile based on the deflection function is relatively straightforward using known models. See, for example, Marcuse, *Principles of Optical Fiber Measurements*, pp. 161–67, Academic Press, New York 1981.

When the diffractive effects increase to a significant level, the known calculation method becomes less reliable and accurate. If the diffractive effects dominate the deflection pattern, the intensity in secondary lobes approaches or exceeds the intensity in the primary lobe for some values of the input position x. In fact, the primary lobe may disappear. In this case, it is difficult, if not impossible, to determine the refractive index profile from the deflection function. This breakdown of the deflection measurement technique is referred to hereinafter as the "striae diffractive effect".

The analysis of the diffractive effects can be motivated by the analogy of a slit grating, even though the OVD process actually produces an extremely complex phase grating. The grating equation is $$m \times \lambda = \alpha \times \sin(\theta)$$

where
m = the order of the pattern, e.g., the number of bright spots = 2m + 1,
$\lambda$ = wavelength, in nm,
$\alpha$ = the striae spacing, in nm, and
$\theta$ = the angle of the order of interest.

To eliminate the diffraction, with m = 1, $\theta$ must be 90°. Therefore, $\alpha$ must be less than or equal to $\lambda$. Therefore, one can eliminate the striae diffractive effect by (a) reducing the spacing between the striae, (b) increasing the measurement wavelength, or (c) some combination of the two.

Decreasing the spacing between the striae can be accomplished in a number of ways. One method is to modify the soot deposition process such that the layers of soot are thinner. This could be accomplished by, for example, increasing the speed of the relative translational movement of the burner along the length of the target rod. However, there are disadvantages to this method, including but not limited to, (a) density variations and (b) manufacturability.

Another method to reduce the spacing between the striae is to neck the canes down to a smaller diameter before analyzing. However, this results in a cane diameter for overcladding which is impractical for commercial purposes. Thus, this method, while useful for providing analytical measurements, is essentially a destructive method which results in waste multimode cane. The procedure by which the necked down cane is produced is laborious, further discouraging its use in a commercial setting. Also, there are advantages in terms of accuracy of the measurement and the bandwidth prediction made therefrom to measure actual canes which will be used to produce preforms as compared to necked down canes which are then discarded.

But the necking down method described above is useful in determining the lower limit for a wavelength at which a cane can be analyzed without the deleterious effects of the striae diffractive effect. Canes of different diameters were analyzed at 632 nm to determine the wavelength at which the striae diffractive effect was eliminated. As a result of this analysis, a scaling factor of 4.55 was developed to determine that the lower limit for a wavelength at which the striae diffractive effect would be eliminated is about 2875 nm.

Because the preforms, canes and fiber drawn therefrom are substantially silica, it was necessary to find a range above 2875 nm in which silica would transmit a substantial portion of the light. Silica is about 80% transmissive in the range of 3000 nm to 3450 nm, and the transmissiveness of silica falls off exponentially for wavelengths longer than about 4000 nm. One practical, and preferred, source in that range is a HeNe laser operating at about 3395 nm. Other sources, such as a $CO_2$ laser operating at about 10,600 nm, could be used. However, these other sources are less convenient to use in an industrial setting because of safety concerns and power absorption by the index matching fluid required for making this measurement.

A problem to be solved in connection with the present invention is a required change in the composition of the refractive index matching fluid. The purpose of the index matching fluid is to minimize the deflection angles which increases the resolution of the calculated refractive index structure. A fluid, available from William Nye Inc. of New Bedford, Mass. under the name DD930929, can be used which transmits about 33% of the power at 3395 nm and which substantially matches the refractive index of the multimode cane.

Figure 4:
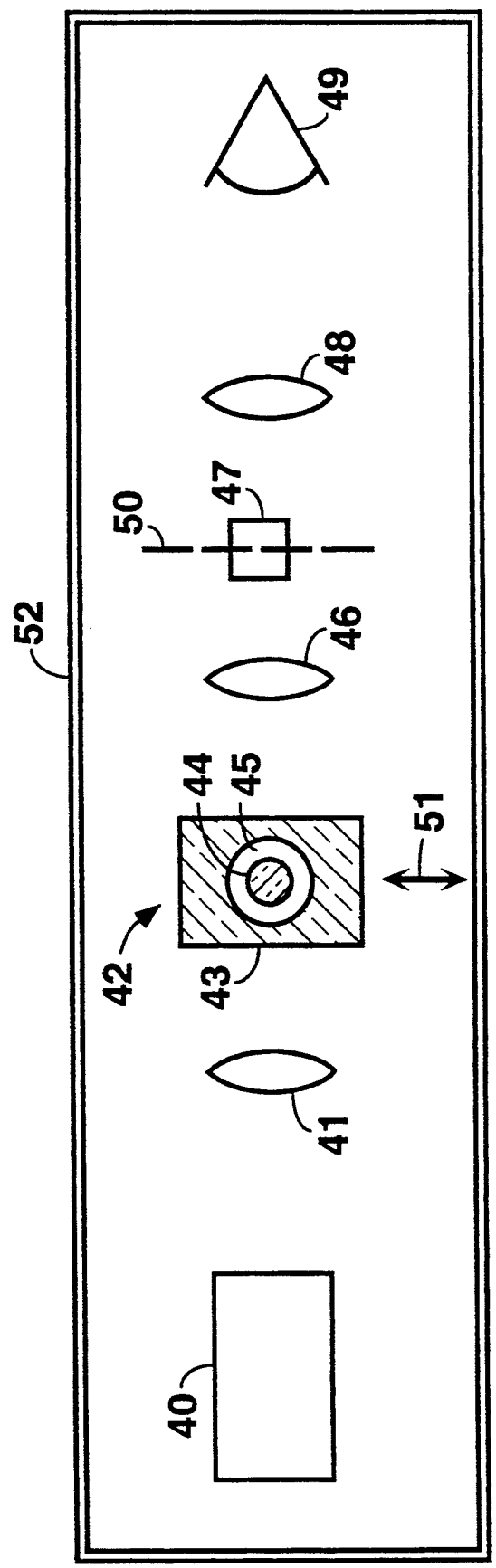
FIG. 4 is a schematic representation of an analyzer according to the present invention.

An exemplary embodiment of an apparatus 52 according to the present invention is described with reference to FIG. 4. A light source 40, preferably operating at about 3395 nm, generates a beam of light which is directed toward input lens 41. The beam is directed toward measurement cell 42 by input lens 41. Cell 42 is preferably a rectangular slab of silica 43, having a constant index of refraction, from the center of which a cylindrical portion 45 has been removed. The sample 44 is held in place in cylindrical portion 45 by well-known means which are not shown. The volume between sample 44 and slab 43 is filled with an index matching fluid such as described above. As the beam passes through the sample, it is deflected and then exits from the opposing side of the cell. The exit angle of the beam is measured by Fourier transforming the beam using a transforming lens 46. The position of the beam is measured in the focal plane of the transforming lens by locating a chopper 47 in the focal plane and modulating the beam such that the phase difference between this beam and a fixed reference beam 50 can be determined using known signal processing techniques. The beam then passes through lens 48 which focuses the beam on detector 49.

Cell 42 is moved in the direction of arrow 51 by a mechanism (not shown) so that the beam is traversed across the cross-section of sample 44 to generate a deflection function. The measurement device is controlled using a computer (not shown), and the signal processing is performed by a data acquisition system (not shown). The deflection function is transformed into the refractive index profile using known mathematical methods such as those disclosed in D. Marcuse, *Principles of Optical Fiber Measurements*, pp. 161–67, Academic Press, New York 1981.

The present invention has been particularly shown and described with reference to the preferred embodiments thereof, however, it will be understood by those skilled in the art that various changes may be made in the form and details of these embodiments without departing from the true spirit and scope of the invention as defined by the following claims. For example, while the present invention has been described herein primarily with reference to the analysis of multimode core cane, the present invention is also applicable to the analysis of multimode core preforms and multimode preforms as well as singlemode core preforms, singlemode core canes and singlemode preforms. Also, although the present invention has been described primarily with reference to preforms produced by the OVD method, it is applicable to preforms or canes made by any method in which striae adversely effect the transmission of light therethrough.

We claim:

1. A method for analyzing an optical fiber core cane, said cane including a series of refractive index striae, comprising
    a. directing a beam of light, said beam having a wavelength, transversely through the cane starting at a first edge of the cane,
    b. detecting the beam after it has passed through the cane,
    c. measuring a deflection of the beam,
    d. indexing the beam relative to the cane by an incremental distance toward a second edge of the cane,
    e. repeating steps a through d until the beam has reached the second edge of the cane to produce a series of deflection measurements, and
    f. reconstructing the refractive index profile of the cane using the series of deflection measurements, wherein the improvement comprises selecting said wavelength to substantially eliminate a diffractive effect caused by said refractive index striae.

2. The method of claim 1 wherein said wavelength is greater than about 2875 nm.

3. The method of claim 2, wherein the wavelength of the beam is in the range of about 3000 to 3450 nm.

4. The method of claim 3, wherein the wavelength of the beam is about 3395 nm.

5. An apparatus for analyzing a core cane with a refractive index profile, comprising
    a. an analyzer cell, said analyzer cell comprising a silica plate with first and second edges and with a hole machined in the center thereof, means for holding the core cane substantially centered in the hole in said plate such that an annular space is provided between said cane and said plate,
    b. means for filling said annular space with an index matching fluid,
    c. means for directing a collimated beam of light produced by a light source, said light source operating at a wavelength, through said first edge of said plate, said beam passing through said plate such that it is transversely incident on the cane,
    d. means for relative movement between said beam and said first edge of said plate,
    e. means for measuring the distance from a central axis of said plate to a point of incidence of said beam on said first edge of said plate,
    f. means for detecting said beam after said beam has exited said cell through said second edge,
    g. means for measuring the distance from a central axis of said plate to a point of incidence of said beam on said means for detecting said beam,
    h. means for collecting and analyzing the distance from step g as a function of the distance from step e to produce a representation of the refractive index profile of the cane, wherein the improvement comprises operating said light source at a wavelength greater than about 2875 nm.

6. The apparatus of claim 5, wherein the wavelength of said light source is in the range of about 3000 nm to 3450 nm.

7. The apparatus of claim 6, wherein the wavelength of said light source is about 3395 nm.

8. The apparatus of claim 7, wherein the light source is a HeNe laser.

* * * * *